US010596330B2

(12) United States Patent
Medina et al.

(10) Patent No.: US 10,596,330 B2
(45) Date of Patent: Mar. 24, 2020

(54) RESORBABLE, DRUG-ELUTING SUBMUCOSAL TURBINATE IMPLANT DEVICE AND METHOD

(71) Applicant: Medtronic Xomed, Inc., Jacksonville, FL (US)

(72) Inventors: Jennifer G. Medina, Jacksonville, FL (US); Drew P. Amery, Jacksonville, FL (US); Dana A. Oliver, Jacksonville, FL (US); Jie Wen, St. Johns, FL (US)

(73) Assignee: MEDTRONIC XOMED, INC., Jacksonville, FL (US)

( * ) Notice: Subject to any disclaimer, the term of this patent is extended or adjusted under 35 U.S.C. 154(b) by 903 days.

(21) Appl. No.: 14/836,594

(22) Filed: Aug. 26, 2015

(65) Prior Publication Data

US 2017/0056602 A1 Mar. 2, 2017

(51) Int. Cl.
*A61M 5/32* (2006.01)
*A61K 9/00* (2006.01)
(Continued)

(52) U.S. Cl.
CPC .......... *A61M 5/3287* (2013.01); *A61B 17/24* (2013.01); *A61B 17/3468* (2013.01);
(Continued)

(58) Field of Classification Search
CPC ....... A61K 9/0024; A61L 31/16; A61L 27/54; A61L 27/58; A61L 31/148;
(Continued)

(56) References Cited

U.S. PATENT DOCUMENTS 3,371,069 A 2/1968 Miyamae et al.
3,416,530 A 12/1968 Ness
(Continued)

FOREIGN PATENT DOCUMENTS

EP 0 080 614 11/1997
EP 0 808 614 A2 11/1997
(Continued)

OTHER PUBLICATIONS

Photo Release—Intersect ENT Announces Positive Data From Clinical Trial of New In-Office Implant for Recurrent Chronic Sinusitis, Annual American Rhinologic Society Meeting, 5 pages (Sep. 22, 2014).
(Continued)

*Primary Examiner* — Brandy S Lee
(74) *Attorney, Agent, or Firm* — Patterson Thuente Pedersen, P.A.

(57) ABSTRACT

Implants are placed in turbinate mucosal tissue using a surgical device having a proximal grip portion and a distal hollow sharp needle portion that is manipulated using the grip portion and inserted submucosally into mucosal turbinate tissue. One or more biodegradable, drug-eluting solid implants are disposed within the needle. The implants have one or more implant withdrawal-discouraging, mucosal tissue-engaging surface features along their length. An actuator disposed within the device is used to deliver one or more of the implants from the needle into the mucosal turbinate tissue and submucosally bury at least one such tissue-engaging feature therein.

23 Claims, 4 Drawing Sheets (51) Int. Cl.
  *A61L 31/16* (2006.01)
  *A61B 17/34* (2006.01)
  *A61B 17/24* (2006.01)
(52) U.S. Cl.
  CPC .......... *A61K 9/0024* (2013.01); *A61L 31/16* (2013.01); *A61M 5/3286* (2013.01); *A61M 2205/04* (2013.01); *A61M 2210/0681* (2013.01)
(58) Field of Classification Search
  CPC ...... A61M 2205/04; A61M 2210/0681; A61M 5/3286; A61M 5/3287; A61B 17/00; A61B 17/24; A61B 17/3468; G01N 2223/419; G01N 23/046; G06T 19/20; G06T 2207/10072; G06T 2207/30136; G06T 2207/30164; G06T 7/0004
  See application file for complete search history.

(56) References Cited

U.S. PATENT DOCUMENTS

| | | | |
|---|---|---|---|
| 3,551,556 | A | 12/1970 | Kliment et al. |
| 3,636,956 | A | 1/1972 | Schneider |
| 3,736,646 | A | 6/1973 | Schmitt et al. |
| 3,903,893 | A | 9/1975 | Scheer |
| 3,935,859 | A | 3/1976 | Doyle |
| 3,948,254 | A | 4/1976 | Zaffaroni |
| 4,249,531 | A | 2/1981 | Heller et al. |
| 4,450,150 | A | 5/1984 | Sidman |
| 5,234,456 | A | 8/1993 | Silvestrini |
| 5,246,455 | A | 9/1993 | Shikani |
| 5,336,163 | A | 8/1994 | DeMane et al. |
| 5,512,055 | A | 4/1996 | Domb et al. |
| 5,543,156 | A | 8/1996 | Roorda et al. |
| 5,545,208 | A | 8/1996 | Wolff et al. |
| 5,633,000 | A | 5/1997 | Grossman et al. |
| 5,762,638 | A | 6/1998 | Shikani et al. |
| 6,280,467 | B1 | 8/2001 | Leonhardt |
| 6,306,424 | B1 | 10/2001 | Vyakarnam et al. |
| 6,431,174 | B1 | 8/2002 | Knudson et al. |
| 6,447,540 | B1 | 9/2002 | Fontaine et al. |
| 6,565,597 | B1 | 5/2003 | Fearnot et al. |
| 6,582,458 | B1 | 6/2003 | White et al. |
| 6,821,297 | B2 | 11/2004 | Snyders |
| 7,041,308 | B2 | 5/2006 | Shalaby et al. |
| 7,074,426 | B2 | 7/2006 | Kochinke |
| 7,264,822 | B2 | 9/2007 | Shalaby et al. |
| 7,361,168 | B2 | 4/2008 | Makower et al. |
| 7,544,192 | B2 | 6/2009 | Eaton et al. |
| 7,547,323 | B2 | 6/2009 | Lavigne |
| 7,618,447 | B2 | 11/2009 | Case et al. |
| 7,654,997 | B2 | 2/2010 | Makower et al. |
| 7,678,144 | B2 | 3/2010 | Bailey et al. |
| 7,815,928 | B2 | 10/2010 | Cherif Cheikh |
| 7,867,547 | B2 | 1/2011 | Tochterman et al. |
| 7,951,135 | B2 | 5/2011 | Eaton et al. |
| 8,016,877 | B2 | 9/2011 | Seguin et al. |
| 8,025,635 | B2 | 9/2011 | Eaton et al. |
| 8,088,404 | B2 | 1/2012 | Udipi et al. |
| 8,092,443 | B2 | 1/2012 | Bischoff |
| 8,192,450 | B2 | 6/2012 | Gonzales et al. |
| 8,226,603 | B2 | 7/2012 | Von Oepen et al. |
| 8,277,477 | B2 | 10/2012 | Oberle |
| 8,337,454 | B2 | 12/2012 | Eaton et al. |
| 8,535,707 | B2 | 9/2013 | Arensdorf et al. |
| 8,585,731 | B2 | 11/2013 | Abbate et al. |
| 8,668,703 | B2 | 3/2014 | Sullivan et al. |
| 8,740,929 | B2 | 6/2014 | Gopferich et al. |
| 8,979,789 | B2 | 3/2015 | Becker |
| 2002/0111603 | A1* | 8/2002 | Cheikh ............... A61D 7/00 604/891.1 |
| 2003/0130726 | A1 | 7/2003 | Thorpe et al. |
| 2003/0236573 | A1* | 12/2003 | Evans ............... A61L 27/12 623/23.58 |
| 2005/0154412 | A1 | 7/2005 | Krueger et al. |
| 2006/0106361 | A1 | 5/2006 | Muni et al. |
| 2007/0014830 | A1 | 1/2007 | Tijsma et al. |
| 2007/0027526 | A1 | 2/2007 | Demetriades et al. |
| 2007/0110788 | A1 | 5/2007 | Hissong et al. |
| 2007/0243225 | A1* | 10/2007 | McKay ............... A61K 9/0024 424/423 |
| 2007/0264310 | A1 | 11/2007 | Hissong et al. |
| 2007/0276468 | A1 | 11/2007 | Holzer et al. |
| 2007/0293946 | A1 | 12/2007 | Gonzales et al. |
| 2008/0140172 | A1 | 6/2008 | Carpenter et al. |
| 2008/0195192 | A1 | 8/2008 | Parsonage |
| 2008/0262598 | A1 | 10/2008 | Elmaleh |
| 2008/0319424 | A1 | 12/2008 | Muni et al. |
| 2009/0044814 | A1* | 2/2009 | Iancea ............... A61B 17/06109 128/848 |
| 2009/0088728 | A1 | 4/2009 | Dollar et al. |
| 2009/0306624 | A1* | 12/2009 | Arensdorf ........... A61K 9/0043 604/506 |
| 2010/0239632 | A1 | 9/2010 | Walsh |
| 2011/0111006 | A1 | 5/2011 | Wong et al. |
| 2011/0125091 | A1 | 5/2011 | Abbate |
| 2011/0125092 | A1 | 5/2011 | Hepworth et al. |
| 2011/0150966 | A1 | 6/2011 | Chen et al. |
| 2012/0046756 | A1 | 2/2012 | Wang et al. |
| 2012/0078377 | A1 | 3/2012 | Gonzales et al. |
| 2012/0083871 | A1 | 4/2012 | Ryan |
| 2012/0323227 | A1 | 12/2012 | Wolf et al. |
| 2013/0006293 | A1 | 1/2013 | Smith |
| 2013/0030545 | A1 | 1/2013 | Gross et al. |
| 2013/0066358 | A1 | 3/2013 | Nalluri et al. |
| 2014/0018839 | A1 | 1/2014 | Renner et al. |
| 2015/0100133 | A1 | 4/2015 | Xie et al. |

FOREIGN PATENT DOCUMENTS

| | | |
|---|---|---|
| EP | 1 057 460 | 12/2000 |
| EP | 1 057 460 A1 | 12/2000 |
| EP | 2 392 366 A1 | 12/2011 |
| GB | 2 091 554 A | 8/1982 |
| WO | WO 92/15286 | 9/1992 |
| WO | WO 2005/117755 A2 | 12/2005 |
| WO | WO2007/143063 A2 | 12/2007 |
| WO | WO 2010/033943 A1 | 3/2010 |
| WO | 2012/048035 | 4/2012 |
| WO | WO2012/048035 A2 | 4/2012 |
| WO | WO 2013/097261 A1 | 7/2013 |

OTHER PUBLICATIONS

Propel® (mometasone furoate implant, 370 μg), Instructions for Use, Intersect® ENT Inc., 2 pages (2013).

Propel® mini (mometasone furoate implant, 370 μg), Instructions for Use, Intersect® ENT Inc., 2 pages (2014).

Propel™ (mometasone furoate implant, 370 μg), Instructions for Use, Intersect® ENT Inc., 6 pages (2011).

"RE: Premarket Notification Exemption Letter for Ethmoid Sinus Spacer", Acclarent, Inc., 8 pages (Apr. 16, 2007).

Baptista et al., Relieva Stratus®, Treatment for Chronic Rhinosinusitus, Department of ENT, University Clinic of Navarra, University of Navarra. Pamplona (Spain) 1 page (2012).

Cawley, S. et al., Sustained release of a corticosteroid using polymeric implants, Agents and Actions, vol. 19, 3/4, cover page, pp. 234-243 (1986).

Fink, J. L. W., Drug-Eluting Sinus Stent Hits the Market: May help maintain patency after FESS, Article, ENT Today, 4 pages (Dec. 2011).

Hosemann, W. et al., Innovative frontal sinus stent acting as a local drug-releasing system, Eur Arch Otorhinolaryngol, 260: 131-134 (2003).

Min, Y. et al., Application of Polylactic Acid Polymer in the Treatment of Acute Maxillary Sinusitis in Rabbits, Acta Otolaryngol (Stockh), 115: 548-552 (1995).

Min, Y. MD, et al., Mucociliary Activity and Histopathology of Sinus Mucosa in Experimental Maxillary Sinusitis: A Comparison (56) References Cited

OTHER PUBLICATIONS of Systemic Administration of Antibiotic and Antibiotic Delivery by Polylactic Acid Polymer, Laryngoscope, 105 (Aug. 1995).

Piskunov, S.Z. et al., Application of Drugs Based on Polymers in the Treatment of Acute and Chronic Maxillary Sinusitus, 3 pages (1989).

Piskunov, S. et al., The prolongation of drug action in the treatment of diseases of the nose and paranasal sinuses, Rhinology, 31: 33-36 (1993).

Shikani, A.H. MD, A New Middle Meatal Antrostomy Stent for Functional Endoscopic Sinus Surger, Laryngoscope, 104: 638-641 (May 1994).

International Preliminary Report on Patentability from International Application No. PCT/US2016/049030, dated Mar. 8, 2018 (7 pages).

* cited by examiner

RESORBABLE, DRUG-ELUTING SUBMUCOSAL TURBINATE IMPLANT DEVICE AND METHOD

TECHNICAL FIELD

This invention relates to the treatment of sinus conditions including inflammation of the turbinates.

BACKGROUND

The turbinates are soft mucosal tissue ridges which are supported by bony understructure, project into the nasal passages, and help warm and moisturize air flowing through the nose. Swollen or otherwise enlarged turbinates can inhibit or obstruct breathing. Treatment therapies include topical or oral administration of nasal decongestants, steroids, anti-inflammatories or other medicaments, and in some instances the use of surgery to remove, reduce or resection the swollen mucosal or supporting bone tissue.

A variety of drug-eluting biodegradable or non-biodegradable devices have been proposed for insertion into nasal passages and sinus cavities. Typically these devices are exposed to air within the nasal or sinus cavity, and in some instances a suture or other fastener is used to retain the device in place.

SUMMARY OF THE INVENTION

The turbinates are exposed to air and fluids, may vibrate or otherwise move during normal breathing, sneezing or nose blowing, and employ cilia and other natural defenses to remove foreign matter and other debris. These factors may dislodge or help dislodge a drug eluting device. Although drug eluting devices may be placed and retained using sutures, doing so represents an extra step and may cause added trauma.

The invention provides in one aspect a surgical device comprising:
(a) a proximal grip portion configured to be grasped outside a patient;
(b) a distal hollow sharp needle portion configured to be manipulated using the grip portion and inserted submucosally into mucosal turbinate tissue in the patient;
(c) one or more biodegradable, drug-eluting solid implants disposed within the hollow needle portion, the implants having a length along the hollow needle portion, and one or more implant withdrawal-discouraging, mucosal tissue-engaging surface features along such length; and
(d) an actuator disposed within the device and configured to deliver one or more of the implants from the hollow needle portion into such mucosal turbinate tissue and submucosally bury at least one such tissue-engaging feature therein.

The invention provides, in another aspect, a method for sinus treatment, the method comprising providing a surgical device comprising:
(a) a proximal grip portion configured to be grasped outside a patient;
(b) a distal hollow sharp needle portion configured to be manipulated using the grip portion and inserted submucosally into mucosal turbinate tissue in the patient;
(c) one or more biodegradable, drug-eluting solid implants disposed within the hollow needle portion, the implants having a length along the hollow needle portion, and one or more implant withdrawal-discouraging, mucosal tissue-engaging surface features along such length; and
(d) an actuator disposed within the device and configured to deliver one or more of the implants from the hollow needle portion into such mucosal turbinate tissue and submucosally bury at least one such tissue-engaging feature therein;
manipulating the grip portion to pierce such mucosal turbinate tissue and submucosally insert the hollow needle portion therein, and activating the actuator to deliver one or more of the implants from the hollow needle portion into such soft tissue and submucosally bury at least one such tissue-engaging feature within such tissue.

BRIEF DESCRIPTION OF THE DRAWING

Like reference symbols in the various figures of the drawing indicate like elements. The elements in the drawing are not to scale.

DETAILED DESCRIPTION

The following detailed description discusses certain embodiments and is not to be taken in a limiting sense. All weights, amounts and ratios herein are by weight, unless otherwise specifically noted.

Figure 1:
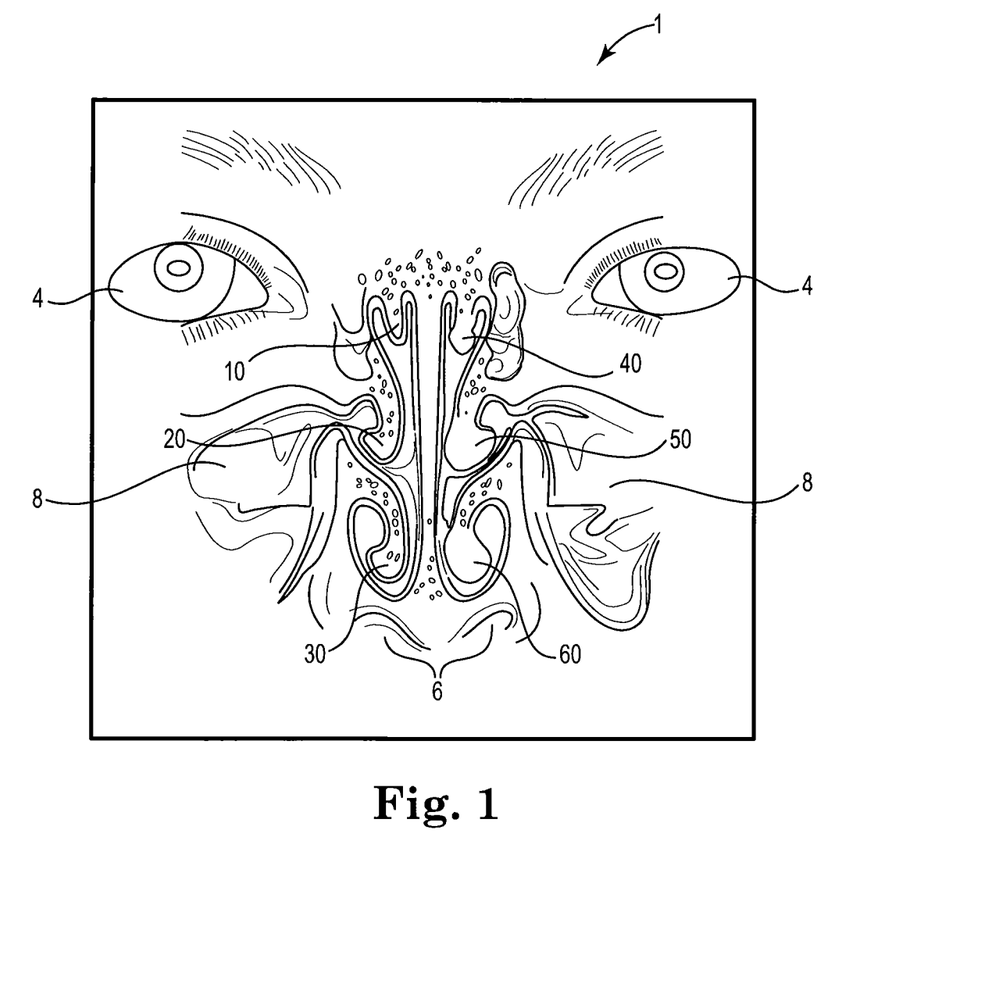
FIG. 1 is a schematic view of the turbinates.

FIG. 1 shows a schematic view of the nasal and sinus passages in human patient 1. Eyes 4 and nostrils 6 are included in the view to assist in visualizing the location and size of maxillary sinuses 8 and nearby turbinates 10, 20, 30, 40, 50 and 60. Superior turbinate 10, middle turbinate 20 and inferior turbinate 30 are located on the left side of FIG. 1, and right of the patient midline from the perspective of patient 1, and are in a normal, unswollen condition. Superior turbinate 40, middle turbinate 50 and inferior turbinate 60 are located on the right side of FIG. 1, and left of the midline from the perspective of patient 1, and are each in an abnormal, swollen condition such as may interfere with normal breathing. In an adult human patient with chronic rhinosinusitis (CRS), the turbinates may for example be swollen sufficiently so as to have a thickness of about 1 cm and a length of 3-4 cm. In pediatric human patients with CRS the corresponding dimensions may for example be a thickness of about 0.5 cm and a length of about 2-3 cm. The disclosed surgical devices may for example be sized to fit submucosally within such swollen tissue.

Figure 2:
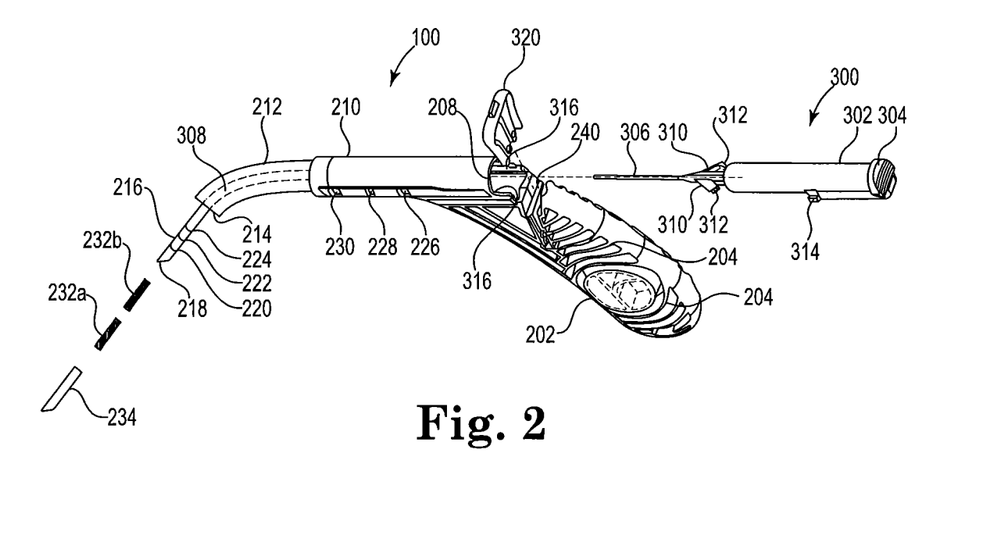
FIG. 2 is an exploded view of a surgical device for implanting the disclosed drug-eluting implants into mucosal turbinate tissue.
Figure 3:
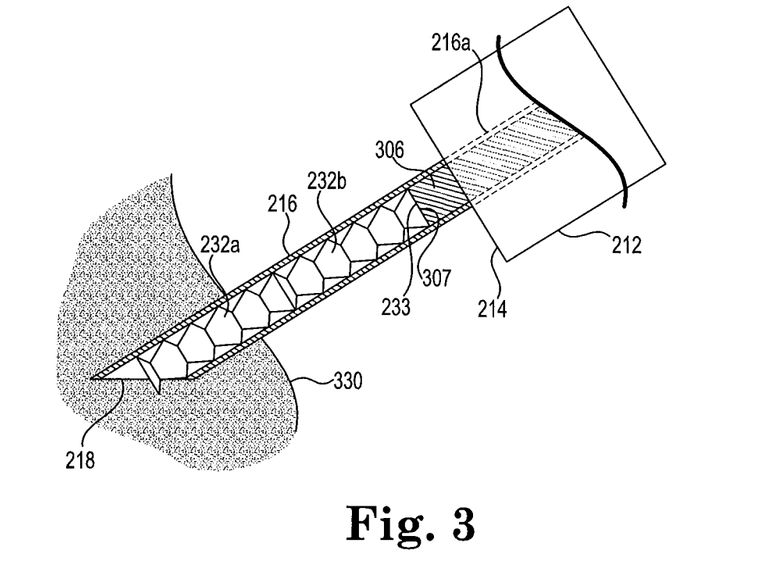
FIG. 3 is a cross-sectional view of the distal needle end of the FIG. 2 device inserted into turbinate tissue and with a plurality of the disclosed drug-eluting implants disposed therein.

Referring to FIG. 2 and FIG. 3, exemplary surgical device 100 may conveniently be made from an injection-molded sterilization-resistant thermoplastic co-molded with a metal needle portion discussed in more detail below. Exemplary thermoplastics include ABS, nylon, polycarbonate, polystyrene and other materials that will be familiar to persons having ordinary skill in the art. Device 100 includes a proximal pistol-grip portion 202 shaped and sized to be received within the gloved palm of a physician. A plurality of optional ribs 204 in handle 202 facilitate uniform distribution of plastic in the molding process and provide an improved gripping surface. Handle 202 is also shaped and sized so that the physician's thumb can readily apply force towards bore opening 208 in barrel 210. Barrel 210 extends from handle 202 and connects with a needle retention and alignment portion 212 which terminates at a distal end 214. Portion 212 may be curved or otherwise bent as shown in FIG. 1 or may have other shapes (e.g., straight) to facilitate manipulation of distal end 214 into position near a target site on a turbinate. Hollow needle 216 projects from distal end 214 and includes a sharp distal tip 218 that can be used to pierce mucosal turbinate tissue. Needle 216 may be straight as shown in FIG. 1 or may have other shapes (e.g., curved or otherwise bent) to facilitate insertion of tip 218 into mucosal turbinate tissue. Optional depth of insertion marks 220, 222 and 224 provide an indicator for judging the extent to which needle 216 has been inserted into tissue.

The length and shape of needle retention and alignment portion 212 and needle 216 may be selected so that device 100 is optimally used to access only one turbinate (e.g., a superior, middle or inferior turbinate) or so that device 100 may be used to access more than one turbinate (e.g., a superior and middle turbinate, a middle and inferior turbinate, or each of a superior, middle and inferior turbinate). Device 100 may also be made in a variety of shapes and sizes, e.g., for human adult, human pediatric or veterinary (e.g., bovine, equine, ovine, porcine, canine or feline) use. Exemplary lengths for needle 216 (including both the visible or exposed portion or needle 216 as well as portion 216a extending into portion 212) may for example be about 5 to about 10 cm for human adult use, about 3 to about 8 cm for human pediatric use, and shorter, similar or longer lengths for veterinary use depending on the chosen animal. The exposed portion of needle 216 may for example have a length of about 2 to about 5 cm or about 2 to about 4 cm for human adult use, about 1 to about 3 cm or about 1 to about 2 cm for human pediatric use, and shorter, similar or longer lengths for veterinary use. Needle 216 may for example have an outer diameter of about 0.23 mm to about 4.6 mm or about 0.23 mm to about 1.7 mm, and an inner diameter of about 0.1 mm to about 3.8 mm or about 0.1 mm to about 1.2 mm, corresponding approximately to Needle Wire Gauge values of 32 gauge to 7 gauge or 32 gauge to 16 gauge.

In the embodiment shown in FIG. 2, barrel 210 includes three openings 226, 228 and 230 along the left side of barrel 210 as viewed by the physician and spaced along its axial dimension, and three optional similar opposing openings (not shown in FIG. 2) on the right side of barrel 210 as viewed by the physician. The FIG. 2 device may be supplied with one or two similar or different implants 232a and 232b shown outside needle 216 in the FIG. 2 exploded view, and shown axially stacked end-to-end inside needle 216 in the FIG. 3 cross-sectional view. Implants 232a and 232b have one or more implant withdrawal-discouraging, mucosal tissue-engaging surface features along their length as is discussed in more detail below. A protective cap 234 may be included with device 100 to cover tip 218.

As will be appreciated by persons having ordinary skill in the art, the embodiment shown in FIG. 2 and FIG. 3 may be modified so as to be supplied to a physician with any desired number of implants, e.g., with three or more implants located axially inside needle 216. The spacing between openings 226 and 228 desirably corresponds to the axial length of implant 232a, and the spacing between openings 228 and 230 desirably corresponds to the axial length of implant 232b. For the embodiment shown in FIG. 2 and FIG. 3, the axial lengths of implants 232a and 232b, the space between openings 226 and 228, and the space between openings 228 and 230 are all the same, but need not be so. Openings 226, 228 and 230 cooperate with slider mechanism 300 to provide one or more and preferably each of visual, audible and tactile feedback to a physician of the progress of an implant or implants through needle 216 as is discussed in more detail below.

Slider mechanism 300 has a generally cylindrical body 302 sized to be slidably received within bore 208. Body 302 includes a proximal thumb tab 304 positioned to be engaged by the thumb of the physician gripping handle 202. Flexible pin 306 extends axially and distally from the distal end of body 302 and is sized to pass through a corresponding bore opening 308 in portion 212, shown in phantom in FIG. 2. One or more flexible lever arms 310 (two are shown in the FIG. 2 embodiment) project laterally and rearwardly from pin 306 and terminate at a latch or latches 312. Locating tab 314, and an optional further locating tab (not shown in FIG. 2) that may be located for example on the right side of slider mechanism 300, project laterally and outwardly from body 302. Latch or latches 312 and tab or tabs 314 are sized to be slidably received by interior recessed slot or slots 316 axially located along the sides of barrel 210. Latch or latches 312 are also sized to expand into and engage openings 226, 228 and 230 and the optional similar openings on the right side of barrel 210 as body 302 travels through bore 208 of barrel 210. Latch or latches 312 are shaped and sized to permit insertion of body 302 into bore 208 and distal advancement of body 302 via thumb pressure on thumb tab 304. When so advanced, body 302 can move from a position in which a latch 312 is engaged in opening 226 to a position in which such latch 312 becomes engaged in opening 228, or from a position in which a latch 312 is engaged in opening 228 to a position in which such latch 312 becomes engaged opening 230. Latch or latches 312 are also shaped and sized so that once a latched position has been reached at openings 226, 228 or 230, body 302 cannot be proximally withdrawn from bore 208 unless latch or latches 312 are pressed inwardly before pulling body 302 from bore 208.

As supplied to the physician, body 302 desirably is already inserted into bore 208 so that latch or latches 312 and tab or tabs 314 ride within recess or recesses 316. Body 302 also desirably is advanced sufficiently far into bore 208 so that the distal end of pin 306 contacts the proximal end of the nearest implant. For example, when only one implant like implant 232a will be provided in device 100, then the distal end of pin 306 may contact the proximal end of such implant. When as is shown in FIG. 3 two implants like implants 232a and 232b are provided in device 100, then the proximal end 307 of pin 306 may contact the proximal end 233 of the most rearwardly-located implant 232b. Latch 312 desirably engages opening 228 when only one implant is provided in device 100 as supplied to the physician, and desirably engages opening 226 when two implants are provided in device 100 as supplied to the physician. Similar engagement desirably is present if the above-mentioned optional right side latches and openings are employed. A removable lockplate 320 may also be provided in device 100 to block or otherwise prevent or limit accidental advancement of body 302 into barrel 210 until such time as the physician is ready to use device 100.

Device 100 normally will be provided to the physician in sterile packaging such as a sealed and suitably irradiated vial, pouch, bag, box or tray. When the time comes for a physician to use device 100 in a surgical procedure, device 100 is removed from such packaging, cover 234 and lock 320 are removed if present, needle 216 and portion 212 are inserted into one of the nares and grip 202 is manipulated so that needle 216 pierces the desired turbinate mucosal tissue target area. For example, FIG. 3 shows needle 216 partially inserted into turbinate tissue 330, at an insertion depth of about one-half the length of implant 232a. Insertion guides 220, 222 and 224 may be employed to judge how deeply tip 218 should be inserted submucosally so as to provide a desired depth of implant insertion. When the desired depth is reached, the physician may press thumb tab 304 towards the distal end of device 100, causing latch 312 to vacate its current opening 226 or 228 and travel axially towards the next opening 228 or 230, and causing the distal end of pin 306 to force implant 232a or 232b through needle 216 and out of needle tip 218 so as to bury submucosally at least a portion containing a tissue-engaging feature, and more preferably a majority and most preferably all of the length such implant, into the target turbinate mucosal tissue. Upon departure of latch 312 from its current opening 226 or 228, the physician will receive visual, audible or tactile indication that implantation of the distal end of the implant into the tissue has commenced. Partial submucosal burying of the implant may be carried out by inserting enough of the implant into the target tissue to submucosally bury at least one tissue-engaging feature therein while holding needle 216 at a desired insertion depth less than the length of the implant (e.g., at depth indicator 220 or 222), halting pressure upon thumb tab 304 before latch 312 reaches the next opening 228 or 230, and then withdrawing needle 216 from the target tissue so that the implant remains behind and partially projects from the target site into the surrounding air-filled cavity. Complete submucosal burying of an implant, or submucosal burying of more than one implant in a single insertion site, may be carried out for example by inserting needle 216 to a desired insertion depth (which may be but need not be a depth greater than the implant length), pressing thumb tab 304 until latch 312 arrives at the next opening 228 or 230 while holding needle 216 at the desired insertion depth, and then withdrawing needle 216 from the tissue so that the implant or implants remain behind, completely buried, and entirely in contact with the surrounding turbinate tissue. The physician may be aided in doing so by the visual, audible or tactile indication provided by arrival of a latch or latches 312 at the next opening 228 or 230, which indication will also signal that the proximal end of the implant has exited needle 216 via tip 218 and that pressure upon thumb tab 304 may be halted. If desired, such pressure may be continued to further advance body 302 and cause another implant to exit needle 216 and become wholly or partly buried in the target tissue site.

If only one or less than all the implants in the disclosed surgical device have been used, device 100 may if desired be removed from the patient and discarded. Alternatively, needle 216 may be moved to a new target site (e.g., from a superior turbinate to the middle turbinate or to another site on the initial target turbinate) so that any remaining implant or implants may be submucosally buried at the new target site. Desirably however this is done while taking appropriate care to avoid microbial cross-contamination between target sites. Consequently the disclosed device preferably is used to bury multiple implants within only a single turbinate.

The disclosed surgical device may be modified in a variety of ways. In place of the disclosed pistol grip device, other configurations such as a finger grip device or a power-assisted device may be employed. Endoscopic, luminescent, electromagnetic, magnetic, radiographic or other navigation aids may be added to the device to aid in positioning the device and its needle tip. For example, a miniature light-emitting diode may be added to distal end 214 and employed as an endoscopic illumination or external transillumination aid to help position needle tip 218 near the desired target area. Lumens to provide features such as irrigation, suction, administration of local anesthetic or the removal of biopsy samples may also be added to the device. A larger-diameter trocar may be used in place of a smaller-diameter needle such as needle 216. Magazines to facilitate loading additional implants may also be employed if desired. Persons having ordinary skill in the art will appreciate that other modifications may be made if desired.

A variety of implants may be employed in the disclosed surgical device. Preferably, the implant includes a biodegradable matrix (for example, a polymeric matrix) with the drug dispersed therein or coated thereon. The biodegradation characteristics of the implant preferably are such that it remains at the implantation site for at least three days, for at least one week, or for at least two weeks. The biodegradation characteristics of the implant also preferably are such that the implant substantially disappears from the implantation site in less than about two months, in less than about one month, or in less than about three weeks. The drug elution characteristics of the implant preferably are such that the drug elutes from the implant for at least three days, for at least one week or for at least two weeks after implantation.

Exemplary matrix polymers include synthetic polymers such as polyesters (for example, polylactides such as polylactic acid or "PLA", poly(lactide-co-glycolide) or "PLGA" copolymers, and cyclic esters such as ε-caprolactone), polyanhydrides, polyorthoesters, polyalkylene glycols (for example, polyethylene glycol or "PEG"), polycarbonates, polyamides, polyphosphoesters, polyphosphazenes and polycyanoacrylates, and natural polymers such as polysaccharides, proteins and nucleic acids. Polyalkylene glycols and PLGA copolymers represent a preferred form of synthetic polymer, and polysaccharides represent a preferred class of natural polymer. Exemplary polysaccharides include agars, alginates, carrageenans, celluloses, chitins, chitosans, chondroitin sulfates, dextrans, galactomannans, glycogens, hyaluronic acids, starches, derivatives (including oxidized polysaccharides and salts) of any of the foregoing, and mixtures of any of the foregoing. The matrix polymer may be uncrosslinked or crosslinked. Additional matrix materials are described in U.S. Patent Application Publication Nos. US 2007/0014830 A1 (Tijsma et al.) and US 2007/0110788 A1 (Hissong et al.). The matrix may include colorants, radiopaque fillers or other additives to aid in visualization or navigation.

A variety of drugs may be used in the disclosed implant. Preferred drugs are useful for the treatment of nasal and sinus conditions and include angiotensin convertin enzyme (ACE) inhibitors; angiotensin receptor blockers (ARBS); antihistamines; steroidal or non-steroidal anti-inflammatory agents; chymase inhibitors; cyclooxygenase-2 (COX-2) inhibitors; decongestants; matrix metalloproteinase (MMP) inhibitors (e.g., doxycycline, TIMP metallopeptidase inhibitor 1 and dexamethasone); mucolytics; therapeutic polymers and combinations thereof. Additional examples of these and other drug classes and drugs are listed in the above-mentioned Tijsma et al. and Hissong et al. applications. If desired, other therapeutic agents for the treatment or prevention of various conditions may be employed, including analgesics, anti-cholinergics, anti-fungal agents, anti-parasitic agents, antiviral agents, biostatic compositions, chemotherapeutic/antineoplastic agents, cytokines, hemostatic agents (e.g., thrombin), immunosuppressors, nucleic acids, peptides, proteins, vasoconstrictors, vitamins, mixtures thereof, and additional other therapeutic agents that will be familiar to persons having ordinary skill in the art. A useful list of such other therapeutic agents may be found, for example, in U.S. Patent Application Publication No. US 2007/0264310 A1 (Hissong et al.). The implant may consist of or consist essentially of the drug, or the drug and other therapeutic agent, or may consist of or consist essentially of the above-mentioned matrix and drug, or the matrix, drug and other therapeutic agent. When a matrix is employed, the drug or drug and other therapeutic agent may be impregnated into or dispersed within the matrix, or the surface of the matrix may be dip coated, spray coated, conjugated with or otherwise covered with or bound to the drug or the drug and other therapeutic agent.

Exemplary lengths for the disclosed implants may for example be about 1 mm to about 2 cm or about 1 mm to about 1 cm for human adult use, about 1 mm to about 1 cm or about 1 mm to about 7 mm for human pediatric use, and about 1 mm to about 4 cm or about 1 mm to about 3 cm for veterinary use. Exemplary outer diameters for the disclosed implants may for example be about 0.1 mm to about 3.8 mm or about 0.1 mm to about 1.2 mm for human adult, human pediatric use or veterinary use.

FIG. 4A through FIG. 4K show several exemplary implants with withdrawal-discouraging, mucosal tissue-engaging surface features. Such features may include projections (e.g., bumps, ribs, hooks or a ratchet rack), recesses (e.g., dimples, grooves or porosity), changes in cross-sectional shape or changes in cross-sectional area along the length of the implant. The implant may be symmetrical or asymmetrical about a central longitudinal axis, they have a generally cylindrical or non-cylindrical e.g. prismatic) shape with respect to such axis, and may have a blunt (e.g., flat), rounded (e.g., domed), sharpened (e.g., pointed) or chiseled (e.g., wedge-shaped) proximal (insertion) end, and a similar or different distal end. The implant may be rigid, or may be compressible with no, slow or rapid recovery of the shape prior to compression. In one embodiment, the withdrawal-discouraging, mucosal tissue-engaging surface features have a configuration such that the work (expressed as a product of force times distance) required to bury the implant submucosally in turbinate tissue is less than the work required to remove the buried implant from such tissue. In another embodiment, the withdrawal-discouraging, mucosal tissue-engaging surface features have a configuration such that the maximum force required to bury the implant submucosally in turbinate tissue is less than the maximum force required to remove the buried implant from such tissue. Preferably at least a majority of implant volume and more preferably all of the implant volume is buried in and contacts turbinate tissue after implantation. In one embodiment, the implant is not tensioned after implantation. In another embodiment, the implant does not draw tissue together after implantation. In yet another embodiment, the implant is not injected into or through and does not contact bone.

Figure 4A:
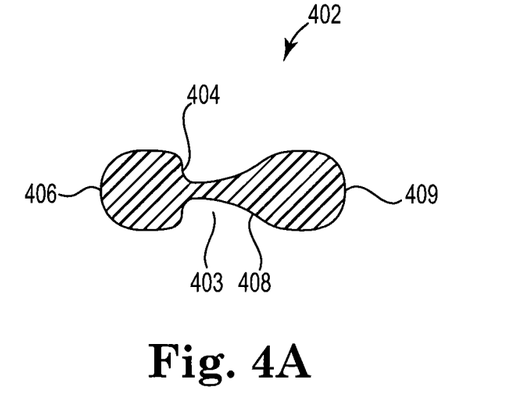
FIGS. 4A through 4K are side sectional views of exemplary drug-eluting implants with a variety of implant withdrawal-discouraging, mucosal tissue-engaging surface features.

FIG. 4A is a cross-sectional view of implant 402 whose central constricted region 403 has a withdrawal-discouraging stop surface 404 near domed distal (insertion) end surface 406 and a gradual tapered surface 408 near proximal (trailing) end surface 409. Implant 402 preferably is made from a relatively stiff biodegradable matrix that will penetrate and laterally displace turbinate tissue when injected therein. After implant 402 has been submucosally buried, nearby displaced tissue preferably returns to the constricted region 403 to provide a tissue-engagement surface adjacent stop surface 404.

Figure 4B:
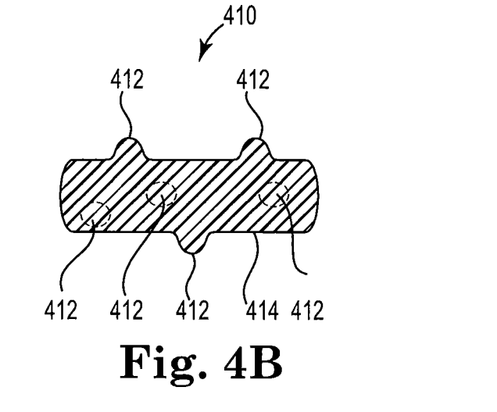

FIG. 4B is a cross-sectional view of implant 410 having a plurality of outwardly-projecting bumps 412 arrayed around the otherwise generally cylindrical surface 414 of implant 410. Bumps 412 provide a withdrawal-discouraging, mucosal tissue-engaging surface feature. Implant 410 may if desired employ a less stiff biodegradable matrix than the matrix used for implant 402, as the design of implant 410 has a substantial minimum diameter and consequently may have better inherent resistance to bending than will be the case for implant 402. The end surfaces of implant 410 may if desired be symmetrical so that either end may serve as the distal (insertion) end surface.

Figure 4C:
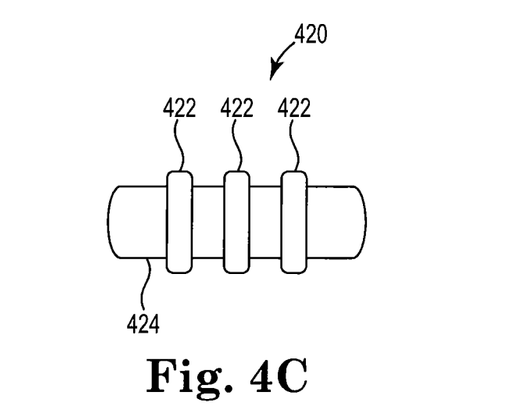
Figure 4D:
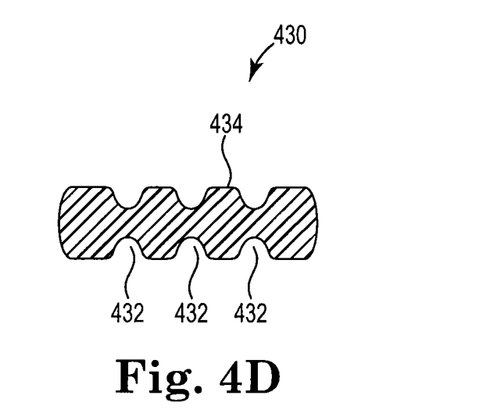
Figure 4E:
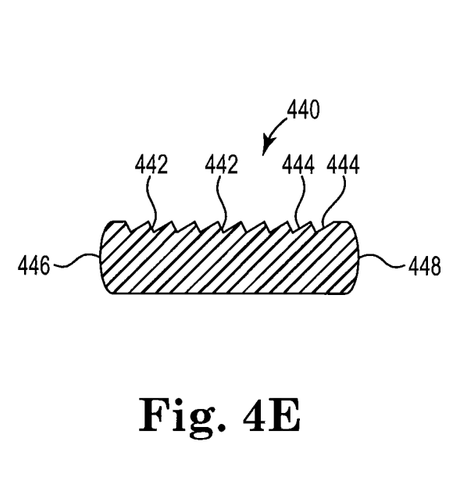

FIG. 4C is a side sectional view of implant 420 having a plurality of outwardly-projecting circumferential ribs 422 arrayed around and along the length of the otherwise generally cylindrical surface 424 of implant 420. FIG. 4D is a cross-sectional view of implant 430 having a plurality of inwardly-directed grooves 432 arrayed around and along the length of the otherwise generally cylindrical surface 434 of implant 430. Both the ribs 422 and grooves 432 provide withdrawal-discouraging, mucosal tissue-engaging surface features.

FIG. 4D is a cross-sectional view of implant 440 having a row of outwardly-projecting asymmetric latches formed by stops 442 and ramps 444 arrayed along the side of implant 440 between distal end surface 446 and proximal end surface 448. The stops 442 and ramps 444 provide withdrawal-discouraging, mucosal tissue-engaging surface features, and are analogous to the ratchet rack in a so-called "zip tie" fastener.

Figure 4F:
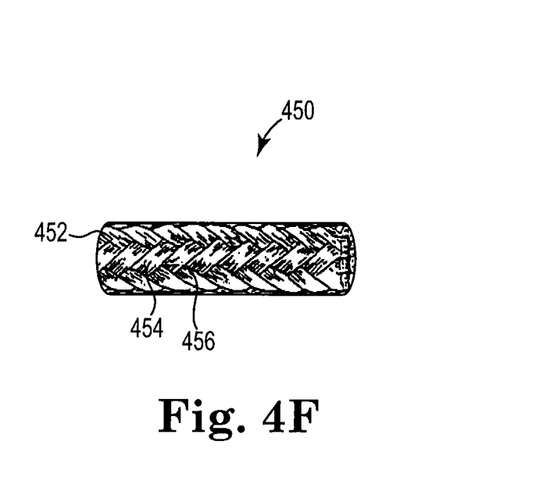

FIG. 4F is a side sectional view of implant 450 having a braided structure formed by fibers such as fibers 452 and 454. Both the exposed outer portion of the fibers and the small depressions such as depression 456 formed where fibers overlap provide withdrawal-discouraging, mucosal tissue-engaging surface features.

Figure 4G:
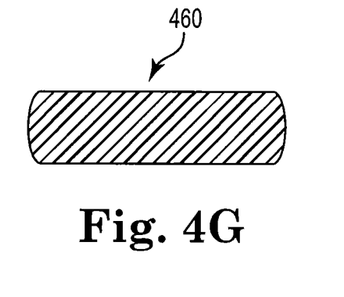
Figure 4H:
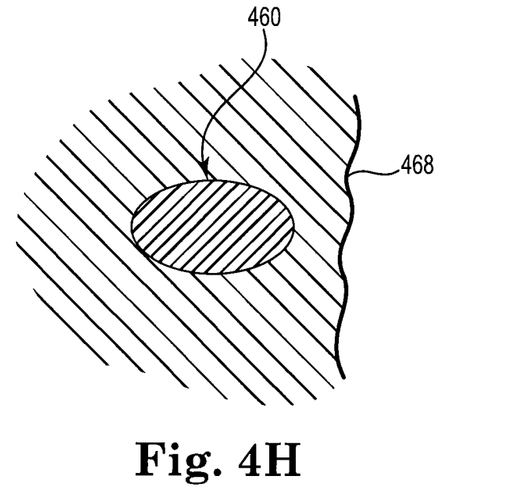

FIG. 4G and FIG. 4H show cross-sectional views of a swellable implant 460 which may as shown in FIG. 4G be generally cylindrical or prismatic prior to injection. As shown in FIG. 4H, after implant 460 has been injected below the surface of turbinate tissue 468, contact with fluids (e.g., water, mucus or blood) present in or near tissue 468 causes implant 460 to become swollen. The resulting increase in implant diameter provides a withdrawal-discouraging, mucosal tissue-engaging surface feature.

Figure 4I:
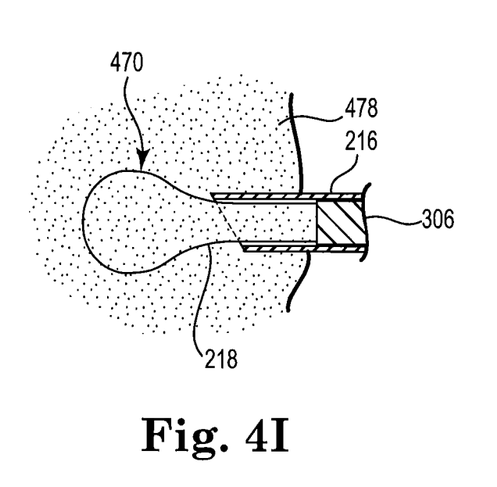

FIG. 4I is a cross-sectional view of a resilient, compressible implant 470 having a reduced diameter when constrained inside needle 216. When injected into turbinate tissue 478, implant 470 expands while in contact with such tissue and assumes its normal unrestrained shape with an expanded diameter. The resulting expanded diameter provides a withdrawal-discouraging, mucosal tissue-engaging surface feature.

Figure 4J:
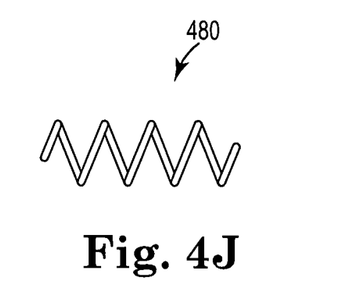

FIG. 4J is a side sectional view of a helical implant 480 that with the aid of a suitable rotating insertion device can be screwed into turbinate tissue. Implant 480 preferably is made from a very stiff biodegradable matrix that can withstand the associated insertion forces.

Figure 4K:
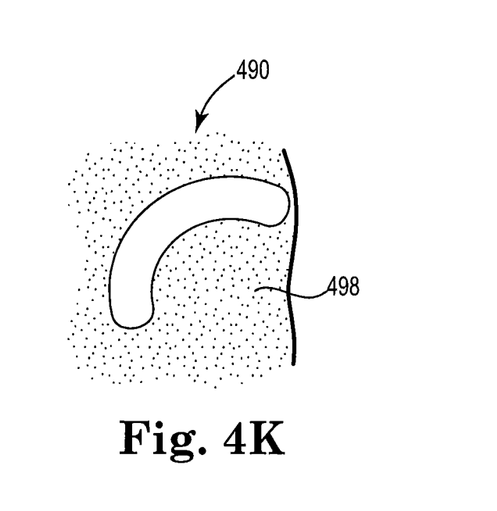

FIG. 4K is a cross-sectional view of a generally curved implant 490 lodged in turbinate tissue 498. Implant 490 may be inserted into such tissue with the aid of a suitably curved insertion needle. If implant 490 has sufficient resiliency and shape memory, it may also be inserted using a straight insertion needle and allowed to assume a curved shape after it exits the needle tip. The curved shape provides a withdrawal-discouraging, mucosal tissue-engaging surface feature.

The complete disclosure of all cited patents, patent applications, technical bulletins and other publications are incorporated herein by reference as if individually incorporated.

Although specific and in some cases preferred embodiments have been illustrated and described, it will be appreciated by those of ordinary skill in the art that a variety of alternate or equivalent embodiments calculated to achieve the same purposes may be substituted for the specific embodiments shown and described above. This application is intended to cover any such adaptations or variations of the embodiments discussed herein. Therefore, it is manifestly intended that this invention be limited only by the claims and the equivalents thereof.

The invention claimed is:

1. A surgical device comprising:
   (a) a proximal grip portion configured to be grasped outside a patient;
   (b) a distal hollow sharp needle portion configured to be manipulated using the grip portion and inserted submucosally into mucosal turbinate tissue in the patient;
   (c) one or more biodegradable, drug-eluting solid implants disposed within the hollow needle portion, the implants having a length along the hollow needle portion, and one or more implant withdrawal-discouraging, mucosal tissue-engaging surface features along the length; and
   (d) an actuator disposed within the device and configured to deliver one or more of the implants from the hollow needle portion into the mucosal turbinate tissue and submucosally bury at least one of the implant withdrawal-discouraging, mucosal tissue-engaging surface features therein.

2. A device according to claim 1 wherein the device contains two or more implants.

3. A device according to claim 1 wherein the device has one or more tabs and openings that provide visible, audible or tactile feedback of the progress of an implant or implants through the needle portion.

4. A device according to claim 1 wherein the device has one or more latches that prevent removal of the actuator.

5. A device according to claim 1 wherein the needle portion is bent.

6. A device according to claim 1 wherein the device is sealed in sterile packaging.

7. A device according to claim 1 wherein the implant comprises a polymeric matrix with a drug impregnated or dispersed therein or coated thereon.

8. A device according to claim 1 wherein the implant degrades in less than one month in mucosal turbinate tissue.

9. A device according to claim 1 wherein the drug elutes from the implant for at least three days and for less than one month.

10. A device according to claim 1 wherein the drug comprises an angiotensin convertin enzyme (ACE) inhibitor; angiotensin receptor blocker (ARBS); antihistamine; steroidal or non-steroidal anti-inflammatory agent; chymase inhibitor; cyclooxygenase-2 (COX-2) inhibitor; decongestant; matrix metalloproteinase (MMP) inhibitor; mucolytic; therapeutic polymer or combination thereof.

11. A device according to claim 1 wherein the drug comprises doxycycline, TIMP metallopeptidase inhibitor 1 or dexamethasone.

12. A device according to claim 1 wherein the one or more implant withdrawal-discouraging, mucosal tissue-engaging surface features include projections.

13. A device according to claim 12 wherein the projections comprise bumps, ribs, hooks or a ratchet rack.

14. A device according to claim 1 wherein the one or more implant withdrawal-discouraging, mucosal tissue-engaging surface features include recesses.

15. A device according to claim 14 wherein the recesses comprise dimples, grooves or porosity.

16. A device according to claim 1 wherein the one or more implant withdrawal-discouraging, mucosal tissue-engaging surface features include a braided structure.

17. A device according to claim 1 wherein one or more implant withdrawal-discouraging, mucosal tissue-engaging surface features are swellable upon exposure to fluid.

18. A device according to claim 1 wherein the implant is not tensioned after implantation.

19. A device according to claim 1 wherein the implant does not draw tissue together after implantation.

20. A device according to claim 1 wherein the implant does not contact bone after implantation.

21. A device according to claim 1 wherein the work, expressed as a product of force times distance, required to bury the implant submucosally in the mucosal turbinate tissue is less than the work required to remove the buried implant from the mucosal turbinate tissue.

22. A device according to claim 1 wherein the maximum force required to bury the implant submucosally in the mucosal turbinate tissue is less than the maximum force required to remove the buried implant from the mucosal turbinate tissue.

23. A method for sinus treatment, the method comprising:
   (a) providing a surgical device comprising:
      (i) a proximal grip portion configured to be grasped outside a patient;
      (ii) a distal hollow sharp needle portion configured to be manipulated using the grip portion and inserted submucosally into mucosal turbinate tissue in the patient;
      (iii) one or more biodegradable, drug-eluting solid implants disposed within the hollow needle portion, the implants having a length along the hollow needle portion, and one or more implant withdrawal-discouraging, mucosal tissue-engaging surface features along the length; and
      (iv) an actuator disposed within the device and configured to deliver one or more of the implants from the hollow needle portion into the mucosal turbinate tissue and submucosally bury at least one of the implant withdrawal-discouraging, mucosal tissue-engaging surface features therein;
   (b) manipulating the grip portion to pierce the mucosal turbinate tissue and submucosally insert the hollow needle portion therein, and
   (c) activating the actuator to deliver one or more of the implants from the hollow needle portion into the mucosal turbinate tissue and submucosally bury at least one such tissue-engaging feature within the mucosal turbinate tissue.

* * * * *